US012635910B2

(12) United States Patent (10) Patent No.: US 12,635,910 B2

De Vries (45) Date of Patent: May 26, 2026

(54) METHOD AND SYSTEM FOR TRACKING OF ACOUSTIC VIBRATIONS USING OPTICAL COHERENCE TOMOGRAPHY

(71) Applicant: Acoustic Insight B.V., Delft (NL)

(72) Inventor: Haaije Rimmer De Vries, Delft (NL)

(73) Assignee: Acoustic Insight B.V., Delft (NL)

( * ) Notice: Subject to any disclaimer, the term of this patent is extended or adjusted under 35 U.S.C. 154(b) by 417 days.

(21) Appl. No.: 18/017,607

(22) PCT Filed: Jul. 23, 2021

(86) PCT No.: PCT/EP2021/070741

§ 371 (c)(1),
(2) Date: Jan. 23, 2023

(87) PCT Pub. No.: WO2022/018285

PCT Pub. Date: Jan. 27, 2022

(65) Prior Publication Data

US 2023/0355139 A1 Nov. 9, 2023

(30) Foreign Application Priority Data

Jul. 24, 2020 (NL) ...................................... 2026138

(51) Int. Cl.
*A61B 5/12* (2006.01)
*A61B 5/00* (2006.01)
(52) U.S. Cl.
CPC .............. *A61B 5/12* (2013.01); *A61B 5/0051* (2013.01); *A61B 5/0066* (2013.01)
(58) Field of Classification Search
CPC ....... A61B 5/12; A61B 5/0051; A61B 5/0066; A61B 2576/02; A61B 5/004; A61B 5/7221; A61B 5/0035
See application file for complete search history.

(56) References Cited

U.S. PATENT DOCUMENTS

2008/0246918 A1* 10/2008 Zhou ...................... A61B 3/102
351/210
2012/0026464 A1* 2/2012 Berger ................... A61B 3/102
351/206

(Continued)

FOREIGN PATENT DOCUMENTS

WO 2017063090 A1 4/2017
WO WO 2019068195 A1 * 4/2019 ............. A61B 5/126

OTHER PUBLICATIONS

Netherlands Search Report dated Apr. 15, 2021, for Netherlands Patent Application No. 2026138.

(Continued)

*Primary Examiner* — Christopher Koharski

*Assistant Examiner* — Steven Maldonado

(74) *Attorney, Agent, or Firm* — Patterson + Sheridan, LLP

(57) ABSTRACT

Method and system for tracking of acoustic vibrations of a structural element of the middle or inner ear with optical coherence tomography using an acoustic source configured to generate an acoustic stimulus to induce vibrations of the structural element; an OCT device configured to measure a measurement signal comprising vibrographic information representative for the vibrations of the structural element in a measurement direction and an optical tracking system arranged to measure a tracking signal representative for displacements of the structural element in at least a tracking direction perpendicular to the measurement direction.

19 Claims, 5 Drawing Sheets

(56) References Cited

U.S. PATENT DOCUMENTS

| | | | |
|---|---|---|---|
| 2013/0060131 A1 | 3/2013 | Oghalai et al. | |
| 2015/0148654 A1 | 5/2015 | Whanwook et al. | |
| 2016/0363435 A1* | 12/2016 | Everett | A61B 3/102 |
| 2017/0251924 A1* | 9/2017 | Koch | A61B 1/051 |
| 2019/0046089 A1* | 2/2019 | Pislak | A61B 5/1076 |
| 2019/0343390 A1* | 11/2019 | Boppart | A61B 1/227 |
| 2020/0037930 A1* | 2/2020 | Abramoff | A61B 5/0066 |
| 2020/0315499 A1* | 10/2020 | Adamson | A61B 5/0066 |
| 2022/0022780 A1* | 1/2022 | Kim | A61B 5/125 |

OTHER PUBLICATIONS

PCT International Search Report and Written Opinion dated Nov. 3, 2021, for International Application No. PCT/EP2021/070741.

* cited by examiner

Fig. 3

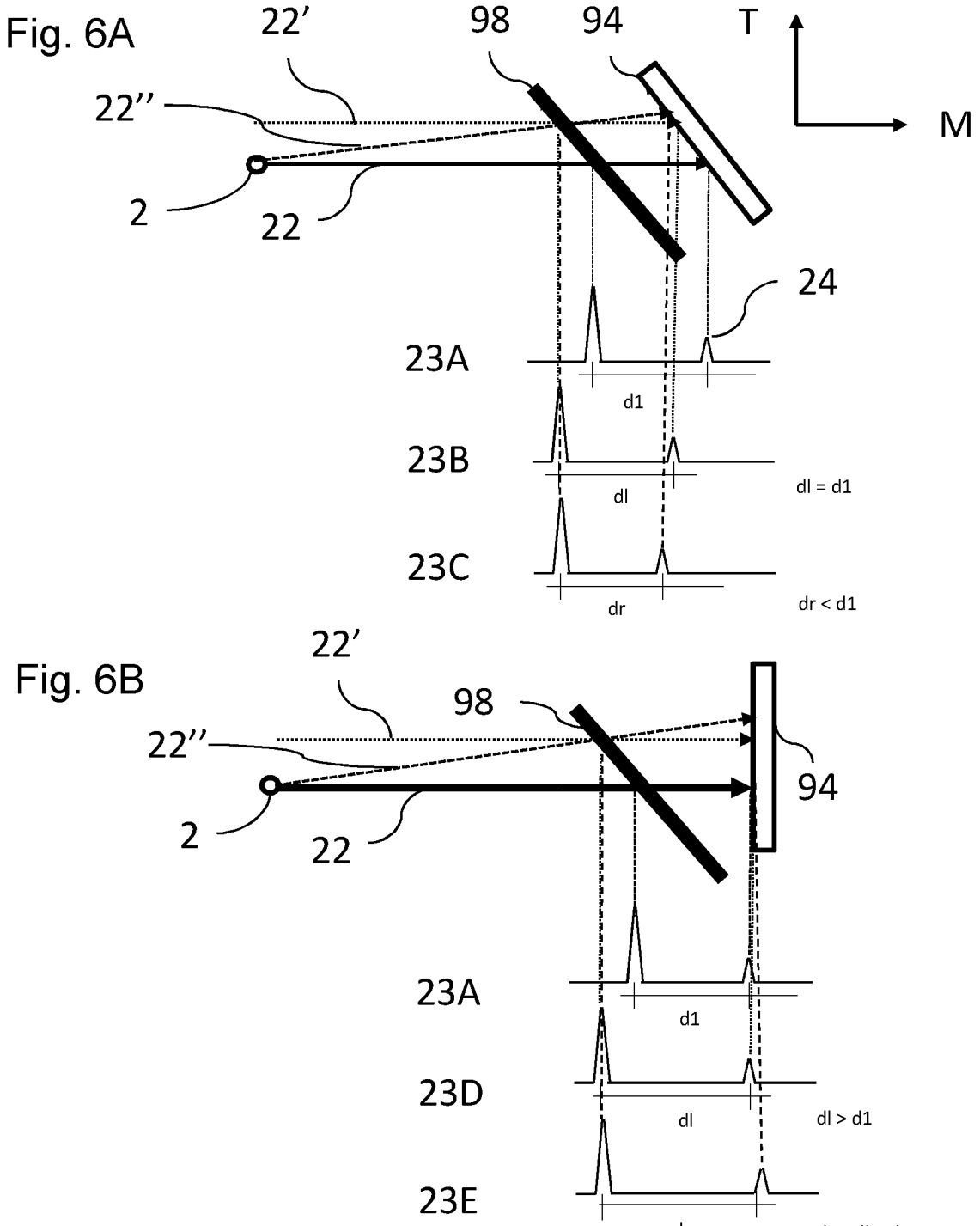

METHOD AND SYSTEM FOR TRACKING OF ACOUSTIC VIBRATIONS USING OPTICAL COHERENCE TOMOGRAPHY

CROSS-REFERENCE TO RELATED APPLICATIONS

This application is a 371 of International Patent Application No. PCT/EP2021/070741, filed Jul. 23, 2021, which claims priority to Netherlands Patent Application No. 2026138, filed Jul. 24, 2020. Each of the aforementioned related patent applications is herein incorporated by reference in its entirety.

FIELD OF THE INVENTION

The present invention relates to a method for tracking of acoustic vibrations using optical coherence tomography, a system for tracking of acoustic vibrations using optical coherence tomography and use of the system for tracking of acoustic vibrations of a structural element in the middle or inner ear.

BACKGROUND OF THE INVENTION

An important part of the auditory organ are the ossicles, which are set in motion by vibrations of the tympanic membrane. The three ossicles (malleus, incus and stapes) amplify frequencies between 20 Hz and 20 KHz and transmit these to the cochlea. The stapes is connected to the cochlea via the oval window and transfers movement to the endolymph and stereocilia.

Patients experience a hearing loss if vibrations are not properly transmitted to the cochlea. This can occur due to various causes: for example, one of the ossicles can be stuck or limited in its movement due to inflammation, proliferation of tissue or bone calcification. Diagnosis of the precise cause is difficult due to the limited accessibility of the middle ear and its position behind the opaque tympanic membrane.

Optical Coherence Tomography (OCT) allows to visualize the structures behind the tympanic membrane, using an optical echo to produce tomographic images that are comparable to black and white images of ultrasound, CT or MRI; albeit with a much higher resolution. In addition to the structural information, OCT can also measure motions by sensing phase differences of reflections of a moving sample, according to the Doppler effect.

WO2017063090 discloses a system and method for swept source optical coherence tomographic vibrography. The system samples the reflectivity depth of a sample along a beam emitted by the OCT system. The OCT beam dwells on a structure of interest for longer periods of time, such that a plurality of measurements can be performed. Each sample is synchronised with the phase of an acoustic stimulus by means of a trigger signal. For tracking the structure of interest, B-mode images can be constructed by directing the OCT beam towards different locations across a field of view.

However, this implies that the vibrographic measurement needs to be interrupted since the OCT beam cannot be directed towards one structure of interest all the time.

Furthermore, structures in the ear are relatively small. For example, the diameter of the incus is 250-600 μm. Aspiration, heartbeat and movements of the patient, as well as movements of the OCT system or user complicate the vibrographic measurements, which may take up to several seconds. Therefore, a precise measurement of the structure of interest may be challenging.

As a result of, inter alia, the interruptions, movements and required precision, measurements can take up a long time. Furthermore, a practical limit is approached where the available acquisition time per image-line, per image-frame approaches the duration of the acoustic period of motion. WO2017063090 requires averaging of samples over multiple image frames, or performing vibrography measurements on selected A-lines, such that B-mode images can be displayed at real-time imaging rates (e.g. >=20 frames/second).

OBJECT OF THE INVENTION

It is an object of the present invention to provide an improved system and method for tracking of acoustic vibrations using optical coherence tomography that lacks one or more of the disadvantages of the prior art, or at least to provide an alternative method and system for tracking of acoustic vibrations using optical coherence tomography The Present Invention The present invention provides a method for tracking of acoustic vibrations using optical coherence tomography according to claim 1.

According to the present invention, a measurement system is provided, comprising an acoustic source, an OCT device and an optical tracking system. A tracking signal may be measured by the tracking system and a measurement signal comprising vibrographic information may be measured by the OCT device. This has the advantage that vibrographic measurements may be performed simultaneously and continuously, without interruptions for structural measurements with the OCT device, as would be required in prior art. Additionally, tracking may be performed continuously during vibrographic measurements, instead of alternated therewith.

The tracking signal is representative for displacements of the structural element in at least a tracking direction. The tracking signal may comprise a 2-dimensional tracking signal, such as an image, a tracking signal from a scanning laser system, such as a SLO system, or another tracking signal, such as a tracking signal from a line scan camera. An image camera may, for example, capture tracking signals at a measurement rate of 50 Hz, which is twice the speed of a B-mode scan in the state of the art. Even higher tracking signal rates, such as 1000 Hz may be obtained with a SLO system, up to 50 000 Hz with a line scan camera, such that relatively small displacements may be detected quickly and that tracking may be performed very precisely.

The tracking system may be configured to measure a tracking signal by measuring displacements of tissue that can be related to displacements of the structural element, such that the tracking signal may be used to adjust the measurement signal. The displacements of tissue may, for example, be displacements of tissue located nearby the structural element, such as displacements of tissue surrounding the structural element. The tissue may additionally or alternatively also be the structural element. This way, the measured measurement signal may be adjusted for influence of displacements of the structural element using the tracking signal.

The tissue may, for example comprise the tympanic membrane, for example a tympanic ring or umbo, as these have been found to provide for reliable tracking due to their accessibility and relatability to other structural elements in the ear.

For practical usage of vibrographic information from measurement signals, a large amount of measurements may be required. Interruptions of the measurements extend the measurement time and increase the probability of measurement errors, e.g. due to noise or tracking errors. It has been found that according to the present invention, vibrographic measurements may be performed much quicker than in the prior art. This improves measurement precision, shortens the required measurement time, and increases comfort for a patient whose ear is to be measured.

In contrast with prior art, adjacent A-line scans of the OCT device do not necessarily have to be stitched together to create structural information, such as B-mode scans for tracking, which potentially saves computational power and may increase capacity for vibrographic measurements.

The measurement signal may be adjusted using the tracking signal at real-time rates, wherein a rate of the tracking system may be adapted independently from a rate of the OCT device.

Furthermore, a tracking signal can be measured by the tracking system, while the tracking system may have specific properties that differ from the properties of the OCT device. For example, focus, contrast and field of view of the tracking system may differ from the OCT device and can therefore be optimised for tracking functionality.

Thus, firstly, the tracking system enables tracking of the structural element during vibrographic measurements, possibly continuously instead of interleaved therewith, enabling continuous vibrographic information from measurement signals. Secondly, tracking may be performed much more precisely than in prior art, for example at real-time measurement rates, or at even higher tracking frequencies, irrespective of a period of motion of the acoustic stimulus. Finally, the measurement signal may be adjusted using the tracking signal.

These properties allow for tracking of acoustic vibrations of a structural element of the middle or inner ear, which may be performed continuously, in an accurate, reliable and precise manner, and which may have improved comfort for users and patients.

The structural element of a patient of which vibrations are to be measured is located in the middle or inner ear. The structural element may, for example, comprise one of the ossicles or a part of the cochlea. In an embodiment, the structural element comprises the tympanic membrane. In other embodiments, the structural element may be the umbo, stapes, incus or the round or oval window or parts thereof.

The acoustic source is configured to generate an acoustic stimulus to induce vibrations of the structural element and may, for example, comprise a tone generator, a speaker or a bone conduction headset. Properties of the acoustic stimulus may be varied with the acoustic source. For example, sound intensity, sound pressure and a direction of the acoustic stimulus may be chosen such that the acoustic stimulus induces vibrations of the structural element. Additionally or alternatively, vibrations of the structural element may be induced by evocations of optoacoustic emissions.

The acoustic stimulus may be a pure-tone stimulus comprising a specific frequency, a broad frequency range and/or a continuous or discrete sequence of frequencies, or a combination thereof.

The OCT device is configured to measure a measurement signal in a measurement direction. The measurement direction is directed towards the structural element to provide vibrographic measurements of the structural element. The measurement direction is normally aligned with an optical axis of the OCT device.

The OCT-device may, in use, emit a beam of low-coherent light using a low-coherent light source. The emitted beam of low-coherent light may then be split in a reference beam and a measurement beam by a beam splitter, such that the reference beam and measurement beam can be reflected by different surfaces. This way, an optical path length based on the distance travelled by the respective beams will depend on the distance of the respective reflecting surface with respect to the beam splitter. Advantageously, the reference beam may be reflected by a reflector arranged at a reference distance. Normally, the measurement beam is emitted along the measurement direction, such that the measurement beam may be reflected by the structural element. As such, the direction of the measurement beam defines the measurement direction.

The term "reflected" as used herein comprises reflected and backscattered.

The optical configuration of the OCT device may be such that an imaging depth of the OCT device is larger than an optical path length difference between the respective beams. The reflected measurement beam and the reflected reference beam may interfere with each other, for example by directing the respective reflected beams such that they coincide.

The detector is configured to detect interference patterns, such that differences between the respective light beams can be measured, such as differences in optical path length and/or phase differences due to vibrations of the structural element. In particular, vibrations of the structural element, such as the tympanic membrane, may result in a phase shift of the reflected measurement beam due to the Doppler effect.

The measurement signal may comprise the detected interference. This way, the measurement signal is representative for vibrations and effects of vibrations on the structural element, such as a amplitude and vibrational frequency of the structural element may be measured on the basis of interference detected by the detector. This provides an extensive amount of data that may be further processed as desired, for example at a later moment.

In an embodiment, the measurement signal may first be pre-processed by filtering, compression and/or fault correction, for example using fixed noise removal, numerical dispersion compensation, zero padding and/or windowing. Pre-processing of the measurement signal may remove artefacts that may degrade the quality of vibrographic information in the measurement signal severely.

Additionally, an inverse Fourier transform may be applied to the measurement signal to extract amplitude and phase components thereof. On the basis of the phase shift comprised in and characteristics of the measurement signal, properties of the structural element and/or other parts of the middle or inner ear may be determined.

The measurement signal, in raw or pre-processed form, may be further processed to extract vibrographic information.

For example, using extracted phase components of the measurement signal, a phase shift development over time may be determined upon multiple measurements, for example upon thousands of detected interference patterns.

The vibrographic information may, for example, be obtained by applying a second Fourier transform to the pre-processed measurement signal wherein the extracted amplitude component is representative for displacements in the measurement direction.

In an embodiment, the vibrographic information is obtained by applying a Fourier transform to the determined phase shift over time, such that an extracted amplitude component is representative for a vibration frequency of the structural element.

In an embodiment, the measurement signal comprises frequencies and/or amplitudes of vibrations, positions and/or speeds of the structural element, processed variants thereof and/or combinations thereof, representative for displacements of the structural element.

The measured measurement signal may be related to the acoustic stimulus. For example, the respective measurement signals may be related to the momentary phase of the acoustic stimulus during a vibrographic measurement. This process is also referred to as 'phase-locking'. A measurement signal may, for example, be related to the momentary acoustic phase of the acoustic stimulus by providing the acoustic phase for each of the measured measurement signals, for example for each of the detected interference patterns.

As a vibration is a back-and-forth movement, the movement of the structural element may describe a sine wave. As a result, displacements measured during an outward movement of the structural element cannot be averaged directly with displacements measured during a backward movement. By phase-locking, measurement signals may be further processed while accounting for the acoustic phase of the acoustic stimulus, for example by averaging signals at acoustic phases of the acoustic stimulus to improve a signal to noise ratio of the measurement signal.

The steps of generating the acoustic stimulus, measuring the measurement signal and the steps of measuring the tracking signal may be performed substantially simultaneously. For example, when measured continuously, these steps may be performed at the same time. Alternatively, when one or multiple of these steps are performed intermittently, the steps of generating the acoustic stimulus, measuring the measurement signal and measuring the tracking signal may be performed alternately in a consecutive manner or simultaneously.

However, during the steps of generating the acoustic stimulus and/or measuring the measurement signal, displacements of the structural element may occur due to other factors than the vibrations induced by the acoustic stimulus. Such displacements may be caused by movements of the OCT device or the acoustic source with respect to the structural element, for example due to movements of a patient.

According to the invention, the tracking signal of the tracking system is used to adjust the measured measurement signal, which may provide for improvement of the signal-to-noise ratio of the measured measurement signal.

The tracking system may comprise a sensor. The tracking system may measure the tracking signal by receiving a tracking beam, for example with the sensor. The tracking beam may comprise light that is reflected by the tracking location. The tracking system may receive a tracking beam of reflected environmental light, reflected light from an external light source and/or the tracking system may also actively emit light that is reflected as a tracking beam.

In an embodiment, the tracking system is arranged to measure a tracking signal representative for displacements of the structural element in a first tracking direction perpendicular to the measurement direction and in a second tracking direction transverse to the first tracking direction and the measurement direction. This way, 2-dimensional tracking may be performed by the tracking system. In a further embodiment, the second tracking direction is arranged perpendicularly to the first tracking direction, such that the first and second tracking direction form an orthogonal basis of a 2-dimensional tracking space.

Adjustment of the measurement signal with the tracking signal may, in an embodiment, be performed substantially simultaneously with the measurements. As such, an adjusted measurement signal may be provided in real time. This allows the corrected signal to be provided to a user immediately.

In an embodiment, the step of using the tracking signal to adjust the measurement signal comprises checking the validity of the measurement signal. The validity may, for example, be checked by comparing a displacement represented in the tracking signal with a predetermined threshold value. In case the displacement exceeds the predetermined threshold value, the measurement signal may be regarded as invalid.

In a further embodiment, a warning may be provided to the user in case the measurement signal is regarded as invalid.

In an embodiment, the step of adjusting the measurement signal comprises correcting the measurement signal in dependence of a displacement of the structural element determined on the basis of the tracking signal. The measured measurement signal may, for example, be corrected during a post-processing step.

Correction may, for example, be performed upon a detected rotation of the structural element. A rotation may result in a different incident angle of the measurement beam with respect to the structural element, causing the reflected measurement beam to have different properties, such as a different phase and/or amplitude of the measurement signal. Thus, correcting for these differences may provide for more accurate data.

The step of correcting may comprise using a model of expected influence of displacements on the measurement signal, wherein the measurement signal is corrected by subtracting respective expected influence for displacements that are represented in the tracking signal.

As an example, the relationship between incident angle of the measurement beam, phase and amplitude of the measurement signal tends to be cosinusoidal. A phase shift of the reflected measurement beam reaches a maximum where the incident angle of the measurement beam is in parallel with a displacement direction of the structural element. Vice versa, the phase shift is normally zero for perpendicular incident angles.

In an embodiment, the step of adjusting the measurement signal comprises adapting the OCT device to compensate for a displacement of the structural element determined on the basis of the tracking signal. The OCT device may be adapted while measuring the measurement signal. As such, the measurement signal may be optimised during vibrographic measurements instead of afterwards in a post-processing step.

In a further embodiment, the OCT device comprises an aiming arrangement, configured to direct the measurement beam and the associated measurement direction towards the structural element. For example, to measure a specific structural element, a measurement beam may be emitted via the aiming arrangement in the measurement direction.

When the structural element is displaced in a tracking direction, the aiming arrangement may adjust the measurement direction of the measurement beam, such that the measurement direction is again directed towards a desired measurement location of the structural element. The aiming arrangement may, for example, comprise a galvo or resonant scanner, that is configured to direct the measurement beam towards the structural element. The aiming arrangement may also comprise a movable mirror, a translation stage, an acousto-optic or electro-optic deflector and/or a liquid spatial light modulator or the like.

Upon large displacements in the measurement direction, such as multiple millimetres, the imaging depth of the OCT device may be exceeded. In an embodiment, the position of an imaging depth window may then be adapted by adapting the optical path length of the reference beam, for example by adapting the reference distance of the reflector.

In an additional or alternative embodiment, the OCT device may be adapted by adapting a focus of the measurement beam. This way, if the structural element is out of a focus of the measurement beam, the focus of the measurement beam may be adapted until the structural element is in focus. The focus may, for example, be varied by, a tuneable lens having a variable power and/or position.

In an embodiment, the step of adjusting the measurement signal comprises discarding a measurement signal obtained when a displacement of the structural element determined on the basis of the tracking signal exceeds a predetermined threshold value. This way, the effect of invalid measured measurement signals on further processing or a provision of a signal to the user may be reduced.

Additionally or alternatively, the measurement of a measurement signal may be interrupted and/or resumed based on the tracking signal. For example, the measurement of a measurement signals may be interrupted when the displacement of the structural element in the tracking direction exceeds the predetermined threshold value, and be resumed when the displacement is below the predetermined threshold value.

In an embodiment, the tracking system is arranged to measure displacements of a predetermined tracking location of the ear in the tracking direction, wherein a position of the predetermined tracking location of the ear is representative for a position of the structural element in the tracking direction. A predetermined tracking location may be a part of tissue, for example a part of the outer or middle ear. By measuring a predetermined tracking location in the tracking direction, tracking may be simplified.

The predetermined tracking location of the ear may, for example, be a part of the tympanic membrane. For example, the predetermined tracking location may be an edge of a tympanic membrane, such as an umbo or a tympanic ring, as the edge may have a high contrast, which may be advantageous to be distinguished by the tracking system.

In an embodiment, the tracking system may be arranged to track multiple tracking locations, such that in addition to movements in the tracking direction, rotations of the structural element may be tracked with the tracking system.

In a further embodiment, multiple tracking locations may be tracked in multiple tracking directions. One or more of the multiple tracking locations may be tracked in the first tracking direction and/or in the second tracking direction.

The predetermined tracking location may be identified by the user, for example by aligning the tracking system with the predetermined tracking location manually. After manual alignment of the tracking system, a tracking signal may be measured.

Additionally or alternatively, the tracking system may be arranged to identify the predetermined tracking location of the ear. The tracking system may comprise an identification arrangement which has been pre-provided with identification characteristics, representative for structural features of predetermined tracking locations. The identification arrangement may be configured to receive structural information, representative for a structure of tissue, from the OCT device or be configured to deduct structural information from the tracking signal. In case the received or deducted structural information matches with the pre-provided identification characteristics, the identification arrangement may activate the tracking system to measure a tracking signal representative for displacements of the structural element.

In an embodiment, the measurement system is further configured to measure a second tracking signal, representative for displacements of the structural element with respect to a second structural element. In this embodiment, the method further comprises a step of measuring a second tracking signal representative for displacements of the structural element with respect to a second structural element, for example displacements parallel to the measurement direction of the OCT device.

By measuring a second tracking signal, tracking of the structural element may be performed, even if the structural element is not directly visible by the tracking system. Especially for certain optical tracking systems, for example a camera or SLO system, the structural element may be obstructed behind another structure, and not be visible by the tracking system. This is, for example the case when tracking certain structural elements are located behind the tympanic membrane.

In an embodiment, a tracking signal may be representative for displacements of the structural element in a first and/or second tracking direction, while the second tracking signal may be representative for displacements of the structural element with respect to a second structural element in another tracking direction, such as in a third tracking direction transverse to the first and second tracking directions. In a further embodiment, the third tracking direction is arranged perpendicularly to the first and second tracking direction. This way, displacements of the structural element may be determined by combining the tracking signal and the second tracking signal, for example by summation of displacements represented in the respective tracking signals.

In an embodiment, the step of using the tracking signal to adjust the measurement signal is performed in further dependence of the second tracking signal. The measurement signal may be adjusted using the tracking signal and the second tracking signal, for example by correcting or discarding the measurement signal and/or adapting the OCT device.

The step of measuring the second tracking signal may, for example, be performed simultaneously with the steps b, c and d of claim 1. This way, the measurement signal may be adjusted on the basis of the second tracking signal in real time.

In an embodiment, the second structural element comprises the tracking location. This way, the tracking signal measured by the tracking system may be representative for displacements of the second structural element in the tracking direction. As such, displacements of the second structural element may be represented in the tracking signal and displacements of the structural element may be determined on the basis of a positional relationship of the second structural element with respect to the structural element represented in the second tracking signal.

In an embodiment, the second tracking signal is representative for displacements of the structural element with respect to a second structural element in the measurement direction. This way, tracking may be performed of a second structural element in a plane that is arranged at a distance from the structural element in the measurement direction.

In an embodiment, the second tracking signal may be representative for rotations of the structural element. Rotations of the structural element, especially rotations around an axis through the structural element, may be relatively difficult to measure with a tracking system alone, for example when the tracking system measures a tracking signal in the plane at a distance from the structural element. Using a second tracking signal, rotations of the structural element may be determined much more precisely.

In an embodiment, the second tracking signal is measured using a second tracking beam, having properties different from the tracking beam, for example regarding wavelength and focus. In a further embodiment, the second tracking beam may be configured to have a lower reflectivity on a surface of the tracking location than the tracking beam of the tracking system.

In an embodiment, the structural element is located further into the ear than the second structural element. In a further embodiment, the second structural element is located in the outer or middle ear, for example a part of the tympanic membrane, and the structural element is located in the middle or inner ear, for example one of the ossicles.

In an embodiment, the OCT device is further configured to measure the second tracking signal. As such, the advantageous properties of the OCT device may be used for measuring the second tracking signal, for example with regard to tissue penetration.

In an embodiment, the measurement signal and the second tracking signal are measured simultaneously using one measurement beam. This way, a second tracking beam may be equal to the measurement beam, and the second tracking signal may be measured using the properties of the measurement beam. This has the additional advantage that no second tracking system may be necessary for measuring the second tracking signal.

Furthermore, if the measurement beam of the OCT device measures a structural element in the middle or inner ear, the measurement beam may pass through tissue of the outer or middle ear in the measurement direction, such as the tympanic membrane, which may be used as second structural element. As such, no additional movement of the measurement beam towards a second structural element may be necessary.

In an embodiment, the OCT device is configured to measure a second tracking signal by measuring a distance between the structural element and a second structural element.

The second tracking signal may comprise the detected interference and may be pre-processed like the measurement signal. Additionally, an inverse Fourier transform may be applied to the second tracking signal to extract amplitude and phase components thereof.

In an embodiment, the second tracking signal comprise amplitude components of interference peaks in the interference detected by the detector. For example, the extracted amplitude components of the second tracking signal may be representative for a positional relationship between the second structural element and the structural element.

In a further embodiment, displacements of the amplitudes in the second tracking signal are representative for displacements of the structural element and the second structural element. In an even further embodiment, displacements of the amplitudes indicate a displacement of the structural element in the measurement and/or tracking direction, wherein the displacement direction may be determined on the basis of the tracking signal.

In an embodiment, the OCT device is further configured to measure a second measurement signal representative for vibrations of a second structural element. The second measurement signal may be measured with the measurement beam, for example when the second structural element is located in a plane away from the structural element in the measurement direction.

By measurement of a second measurement signal, differences in vibrations of the structural element and the second structural element may be determined. For example, vibrations of the structural element may be phase shifted compared to the vibrations of the second structural element, for example be in counter phase with each other.

The second measurement signal may be determined in the same way as the measurement signal, and for example comprise phase shifts at different positions in the measurement direction that are represented in the interference detected, obtained using a Fourier transform thereof. The measurement system may be provided with processing means configured to distinguish interference peaks representative for vibrations of the structural element from interference peaks representative for those of the second structural element.

In an embodiment, a measurement location of the second measurement signal and a tracking location of the tracking signal and/or the second tracking signal on the second structural element are the same.

In an embodiment, the measurement signal, the second measurement signal and the second tracking signal are measured simultaneously using one measurement beam. As such, only one tracking system and one OCT device may be necessary for measuring the tracking signal, the second tracking signal, the measurement signal and the second measurement signal.

In an embodiment, the measurement system is provided with processing means configured to compare the measurement signal and the second measurement signal, for example to determine a ratio.

In a further embodiment, the measurement system may be configured to validate positioning of the measurement beam on the basis of phase differences between the measurement signal and the second measurement signal. The positioning may, for example, be validated by comparing a phase difference between the respected measurement signals with a predetermined expected phase difference.

The structural element may, for example, be located in the inner ear, such as behind a round window. The second structural element may, for example, be the tympanic membrane. In an embodiment, the second structural element is located on the tympanic membrane. The tympanic membrane and structures of the round window may expected to vibrate in counter phase, such that an expected phase difference between the respective measurement signal is maximal.

In an embodiment, the optical tracking system comprises a video camera, thermal camera or scanning laser ophthalmoscope. An optical system may be advantageous for integration with the OCT device.

The optical tracking system may comprise an OCT tracking system. An optical OCT tracking system may be advantageous as a time relation between the OCT tracking system and the OCT device may be defined in the optical configuration of the OCT tracking system.

In a further embodiment, a sensitive wavelength range of the optical tracking system differs from a wavelength range the OCT device. An advantage of a different sensitive wavelength range is that undesired interference between the OCT device and the tracking system may be avoided.

Additionally, wavelengths of the OCT device may be optimised for measuring acoustic vibrations of the structural element, while wavelengths of the tracking system may be optimised for tracking.

For example, the wavelength range of the OCT device may be selected for high transmission through the tympanic membrane. Wavelengths of the OCT device may comprise the near-infrared window, such as 830-1550 nm, where light has its maximum depth of penetration in tissue.

The sensitive wavelength range of the optical tracking system may comprise wavelengths that are absorbed by the tracking location, but less absorbed by surrounding tissue, or vice versa. This way, a high contrast between the tracking location and surrounding, tissue may be obtained.

The sensitive wavelength range of the optical tracking system may, for example be selected for high reflectivity on the tympanic membrane. The sensitive wavelength range of the optical tracking system may comprise 400-750 nm, such as 500-600 nm, for example a wavelength range of green light.

In an embodiment, the tracking beam of the optical tracking system may be optically coupled to the measurement beam. In particular, an OCT tracking system may be optically coupled to the OCT device, by optical coupling of light emitted by the OCT tracking system and the measurement beam using circulators and beam splitters. This way, when the tracking system receives a tracking beam reflected by the tracking location, the tracking beam and the measurement beam may be related in time due to the optical coupling. As such, post-processing for relating the tracking beam and the measurement beam by analysis upon receiving the tracking beam may not be necessary.

In an embodiment, the step of measuring the measurement signal comprising vibrographic information representative for the vibrations of the structural element comprises focusing a measurement beam of the OCT device on the structural element, wherein the step of focusing comprises:

focusing a measurement beam of the OCT device on the structural element, and wherein the step of focusing comprises:

selecting a focusing location, wherein the reflectivity of the focusing location is higher than the reflectivity of the structural element and wherein the focusing location has a predetermined positional relationship with respect to the structural element;

determining a focus setting for the measurement beam with a beam reflected by the focusing location;

adjusting the measurement beam to focus on the structural element using the determined focus setting.

For vibrographic measurements of a structural element in the middle or inner ear, it may be advantageous to obtain a desired focus of the measurement beam of the OCT device on the structural element. This may improve the signal to noise ratio of the measurement beam. However, focusing may be challenging on structural elements having a low reflectivity of the measurement beam. By selecting a focusing location having a higher reflectivity than the structural element, properties of a reflected measurement beam that is reflected by the focusing location may be determined more reliably.

Furthermore, a distance to the focusing location may be determined in dependence of the reflected measurement beam. As the focusing location has a predetermined positional relationship with respect to the structural element, for example a predetermined positional relationship with respect to depth in the measurement direction, a reliable focus setting for measuring the structural element may be determined with a beam reflected by the focusing location.

The beam may, for example, be a beam emitted by the OCT device, for example a beam similar to the measurement beam, such as at a wavelength similar to that of the measurement beam.

The step of determining a focus settings may be performed experimentally by detecting a beam reflected by the focusing location with the detector for different focus settings. As an example, the focus setting having the highest signal to noise ration may be selected.

After determination of the focus setting, the measurement beam may be focused on the structural element with the determined focus setting. Simultaneously or after that, the measurement beam may then be moved to the structural element for vibrographic measurements, for example using an aiming arrangement.

In an embodiment, the structural element is a structural element of the inner ear, for example a structural element behind the round window. As the structural elements of the inner ear may be weak reflectors, measuring these structures may require an optimal focus setting.

In a further embodiment, the focusing location is a bone. A bone may have a relatively high reflectivity and a position that may be obtained reliably, such that a positional relationship with a structural element may be determined.

The invention further provides a system for tracking of acoustic vibrations of a structural element of the middle or inner ear with optical coherence tomography, comprising:

an acoustic source configured to generate an acoustic stimulus to induce vibrations of the structural element;

an OCT device configured to measure a measurement signal representative for the vibrations of the structural element in a measurement direction; and a tracking system arranged to measure a tracking signal representative for displacements of the structural element in at least a tracking direction perpendicular to the measurement direction, wherein the system is configured to perform the steps of:

a. generating an acoustic stimulus with the acoustic source to induce vibrations of the structural element;

b. measuring the measurement signal comprising vibrographic information representative for the vibrations of the structural element;

c. measuring the tracking signal representative for the displacements of the structural element;

d. using the tracking signal to adjust the measurement signal of step b.

The system may be suited for tracking of acoustic vibrations according to embodiments of the method for tracking of acoustic vibrations of a structural element of the middle or inner ear according to the present invention.

The invention further entails the use of the system for tracking of acoustic vibrations of a structural element of the middle or inner ear.

BRIEF DESCRIPTION OF THE DRAWINGS

Further characteristics and advantages of the invention will now be elucidated by a description of embodiments of the invention, with reference to the accompanying drawings, in which:

FIG. 3 schematically depicts movements of a structural element according to an embodiment of the present invention;

FIGS. 6A-6B schematically depict measurement beams of an OCT device according to the embodiment of FIG. 5B.

DETAILED DESCRIPTION OF EMBODIMENTS

Figure 1:
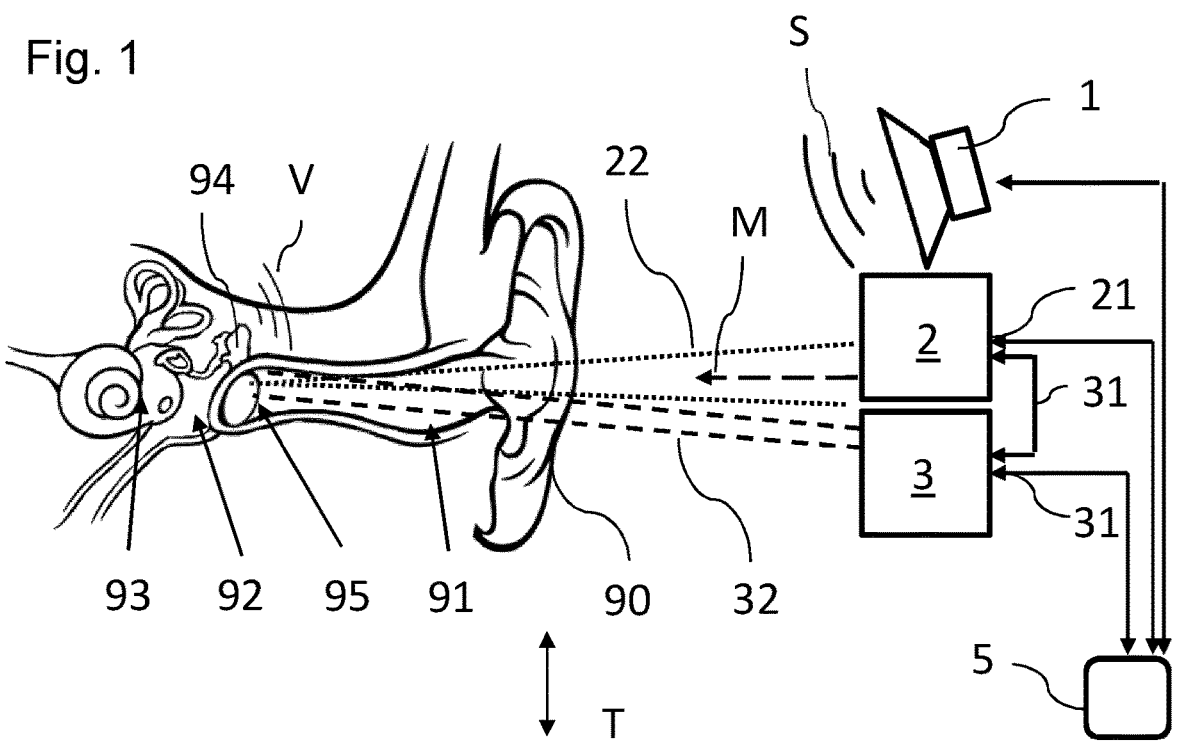
FIG. 1 schematically depicts an embodiment of a system for tracking of acoustic vibrations of a structural element of the middle or inner ear with optical coherence tomography.

FIG. 1 schematically depicts an embodiment of a system for tracking of acoustic vibrations of a structural element of the middle or inner ear with optical coherence tomography. An ear (90) of a patient is depicted, comprising an outer ear (91), middle ear (92) and inner ear (93). The structural element (94) to be measured in this embodiment is the malleus ossicle. By measuring its vibration, properties of the structural element may be determined, which may provide valuable insights into the condition of the auditory system of a patient. Alternatively, acoustic vibrations of other structural elements may be measured, such as the tympanic membrane, umbo, stapes, incus or the round or oval window. Also, specific parts of structural elements may be measured, such as a handle of the malleus.

An acoustic source (1) is provided, configured to generate an acoustic stimulus(S) to induce vibrations (V) of the structural element (94). The acoustic source is a tone generator, configured to generate acoustic frequencies between 20 Hz and 20 kHz.

An OCT device (2) is provided, configured to measure a measurement signal (21), comprising vibrographic information representative for the vibrations (V) of the structural element in a measurement direction (M). The OCT device is configured to emit a measurement beam (22) comprising low-coherent light along an optical axis of the OCT device, which is aligned with the measurement direction (M) and directed towards a structural element (94). The OCT device is configured to receive a reflected measurement beam, which may interfere with a reference beam of the OCT device, such that interference may be detected by a detector of the OCT device.

A tracking system (3) is provided, arranged to measure a tracking signal (31) representative for displacements of the structural element (94) in at least a tracking direction (T) perpendicular to the measurement direction (M). The tracking system is configured to measure a 2-dimensional tracking signal, representative for displacements of a tracking location (95) in the tracking direction (T) and in a second tracking direction which is perpendicular to the measurement direction (M) and the tracking direction (T). In other embodiments, the tracking system (3) may also be configured to measure in the measurement direction.

The OCT device (2) and the tracking system (3) are connected to the processing device (5). The processing device (5) may be a separate device, such as an external processor, a computer or network. Alternatively, the processing device (5) may be partly or completely integrated in the OCT device (2) or the tracking device (3). The acoustic source (1), OCT device (2) and tracking system (3) may be configured to communicate with the processing device (5), for example to send or receive the respective signals, control commands, or other information.

The processing device (5) may be configured to display received signals to a user, to provide a command determining which structural element shall be measured. The command may be pre-programmed in the processing device, or alternatively be selected by a user. The user may for example select the structural element on a structural image of the ear of the patient, which has been captured by performing a B-mode scan with the OCT device. Commands may be provided to the OCT device, for example via the same connection as the vibrographic image signal (21). In this embodiment, the structural element is selected by aiming the device towards the structural element.

The tracking signal (31) may be provided to the OCT device (2) for adjustment of the measurement signal therewith, and/or be provided to the processing device (5).

The tracking location may be determined by the user before performing measurements. The tracking location may also be determined by the tracking system (3), for example by pre-providing a tracking location characteristic in the tracking system.

The tracking system (3) is arranged to identify the predetermined tracking location (95) by capturing structural information, and comparing the structural information with the pre-provided tracking location characteristic.

The tracking system (3) is an optical system. The tracking system (3) receives a tracking beam (32) reflected by the tracking location (95). The tracking system may receive a tracking beam of reflected environmental light, reflected light from an external light source and/or the tracking system (3) may also actively emit light that is reflected as a tracking beam. Thus, the measurement beam (22) and tracking beam may be bidirectional. For example, the measurement beam may be reflected by the structural element (94) as a reflected measurement beam. For clarity, single lines are shown in the Figures.

The tracking signal (31) may be provided to a processing device (5) and/or to the OCT device (2).

A sensitive wavelength range of the tracking system (3) may differ from a wavelength range the OCT device. The wavelength range of the OCT device is selected for high transmission through the tympanic membrane, and the sensitive wavelength range of the optical tracking system is selected for high reflectivity on the tympanic membrane.

In use, an acoustic stimulus(S) is generated with the acoustic source (1) to induce vibrations (V) of the structural element (94). As an example, the tone generator may provide a 1 kHz sound wave at a loudness of 70 dB directed towards the structural element (94).

The OCT device emits a measurement beam (22) in the measurement direction (M), which is directed towards the structural element (94), either manually by an user, for example by rotating the OCT device (2) manually, or automatically by an aiming arrangement and a tuneable lens (for example as in 82, 83 in FIG. 2), such that the measurement beam may be reflected by the structural element.

The measurement beam is reflected by the structural element as a phase-shifted reflected measurement beam, due to the Doppler effect caused by vibrations of the structural element with respect to the reference beam of the OCT device (2). The reflected measurement beam is measured with the OCT device (2). The vibrations (V) and their effects on the structural element (94), such as changes in momentary position and speed of the structural element (94) may be determined on the basis of interference detected by the detector of the OCT device (2).

The OCT device (2) is configured to measure a measurement signal (21). The OCT device provides the measurement signal (21) comprising vibrographic information representative for the vibrations (V) of the structural element (94) to the processing device (5). The OCT device and the processing device (5) are configured to adjust the measurement signal (21) using the tracking signal (31).

At the same time, the tracking system (3) measures displacements of the tracking location (95). The position of the tracking location is representative for a position of the structural element (94) in the tracking direction (T). Changes in position of the tracking location (95) may be caused by movements of the ear (90). In this embodiment, the tracking location comprises tissue of the outer ear (91), such as tissue in the ear canal. Additionally or alternatively, the tracking location may be a single point or a surface and comprise locations anywhere in the ear (90), for example on the tympanic membrane, such as a tympanic ring or umbo. The optical tracking system is a camera, providing the tracking signal at more than 20 Hz, such as for example 50 Hz. Additionally or alternatively, the optical tracking system may be an SLO system or comprise line scan cameras.

The tracking signal (31) is provided to the processing device (5), and to the OCT device (2). The tracking signal (31) is used to adjust the measured measurement signal (21). The measured measurement signal (21) may be adjusted by the OCT device (2) by adjusting the OCT device, for example to adapt a focus of a measurement beam (22), an imaging depth window and/or the measurement direction (M), to compensate for a displacement of the structural element determined on the basis of the tracking signal (31).

Additionally, the measurement signal (21) may be adjusted by the processing device (5) in dependence of the tracking signal (31) by discarding a measurement signal (21) obtained when a displacement of the structural element (94) determined on the basis of the tracking signal (31) exceeds a predetermined threshold value and/or by correcting the measurement signal in dependence of a displacement of the structural element determined on the basis of the tracking signal.

The measurement signal (21) measured by the OCT device (2) comprises detected interference, which is preprocessed by filtering using fixed noise removal, numerical dispersion compensation, zero padding and windowing. Additionally, an inverse Fourier transform is applied to the measurement signal to extract amplitude and phase components thereof.

Using the extracted phase components of the measurement signal, a phase shift development over time is determined by the processing device (5) upon multiple measurements, for example upon receiving measurement signals comprising vibrographic information representative for vibrations (V) of the structural element in the measurement direction (M) during a certain time, for example at least a second, such as multiple seconds.

Subsequently, the vibrographic information is obtained by applying a Fourier transform to the determined phase shift over time, such that an extracted amplitude component is representative for a vibration frequency of the structural element.

Correction and/or discarding the measurement signal (21) may be performed by the processing device (5) and/or the OCT device (2) during any of the steps above.

The vibrographic information is then displayed to the user. Additionally, other information may be displayed, such as unprocessed measurement signals and/or further processing may be performed by the processing device (5). If the measurement signal (21) is at least partially discarded, a measurement signal (21) may be measured for a longer time, such that sufficient data can be collected.

Figure 2:
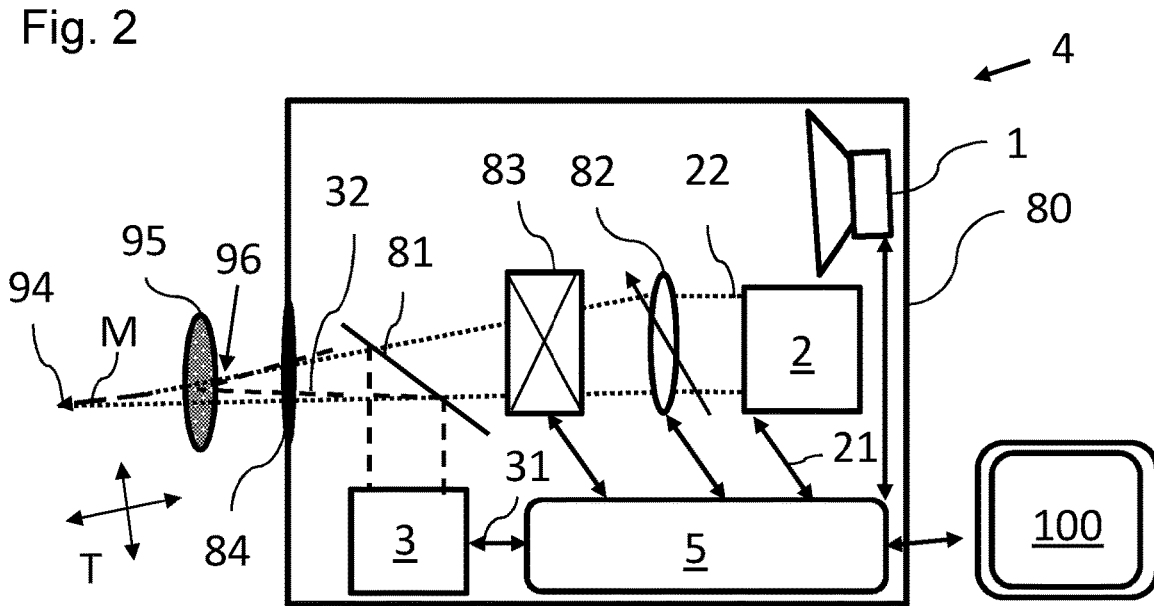
FIG. 2 schematically depicts an embodiment of a measurement system for tracking of acoustic vibrations of a structural element of the middle or inner ear with optical coherence tomography.

FIG. 2 schematically depicts an embodiment of a measurement system (4) for tracking of acoustic vibrations of a structural element of the middle or inner ear with optical coherence tomography. The measurement system, comprising the acoustic source (1), the OCT device (2) and the tracking system (3) is integrated in a single housing (80). The tracking system is a SLO system, capturing tracking signals at a rate of 1000 Hz. In other embodiments, the tracking system may also comprise a line-scan camera or thermal camera. A line-scan camera may capture tracking signals at 50 kHz, at a frequency higher than frequencies of the acoustic stimulus. The frequency may even approach a sampling frequency of the OCT device, for example equal to that of the OCT device, such that very precise tracking becomes possible.

The measurement system (4) comprises a beam splitter (81), which comprises a semi-transparent mirror, such that a measurement beam (22) of an OCT device (2) and a tracking beam (32) of the tracking system (3) may be directed along the same optical axis, such that the tracking beam (32) and the measurement beam (22) are emitted through a single aperture (84). The OCT device comprises a tuneable lens (82), having a variable power, and an aiming arrangement (83), comprising a galvo scanner. The aiming arrangement and tunable lens are shown separately but may also be integrated in the OCT device (2). The aiming arrangement (83) may aim the measurement beam based on input from a user, data from the OCT device (2), based on the tracking signal (31) from the tracking system and/or based on commands from the external device (5).

By actuation of the tuneable lens (82), the lens may be altered in power and/or translated, such that the measurement beam (22) can be directed in a predetermined measurement direction (M) towards the structural element (94). As the tracking beam (32) and the measurement beam (22) are directed along the same optical axis, the tracking direction (T) is determined by aiming the measurement direction (M). Alternatively, the measurement beam (22) and/or the tracking beam (32) may be provided with separate aiming arrangements (83) and/or tunable lenses (82).

The measurement system (4) comprises a processing device (5), configured to control the acoustic source (1), the OCT device (2), the tracking system (3), the aiming arrangement (83), the tuneable lens (82) and an external display (100). The display may alternatively also be located in the housing (80).

The vibrographic measurement signal (21) and the tracking signal (31) are provided to the processing device (5), such that the OCT device may be adapted to compensate for displacements of the structural element by controlling aiming arrangement (83) and the tuneable lens (82) to vary a measurement direction of and/or a focus of the measurement beam. This way, the measurement beam (22) may be directed within 0.1 mm on the structural element (94) during relatively long measurement times of several seconds. The OCT device may also be adapted using other hardware and/or using software, such as autofocus algorithms.

In this embodiment, the tracking location (95) is a point (96) on the tympanic membrane.

Figure 3:
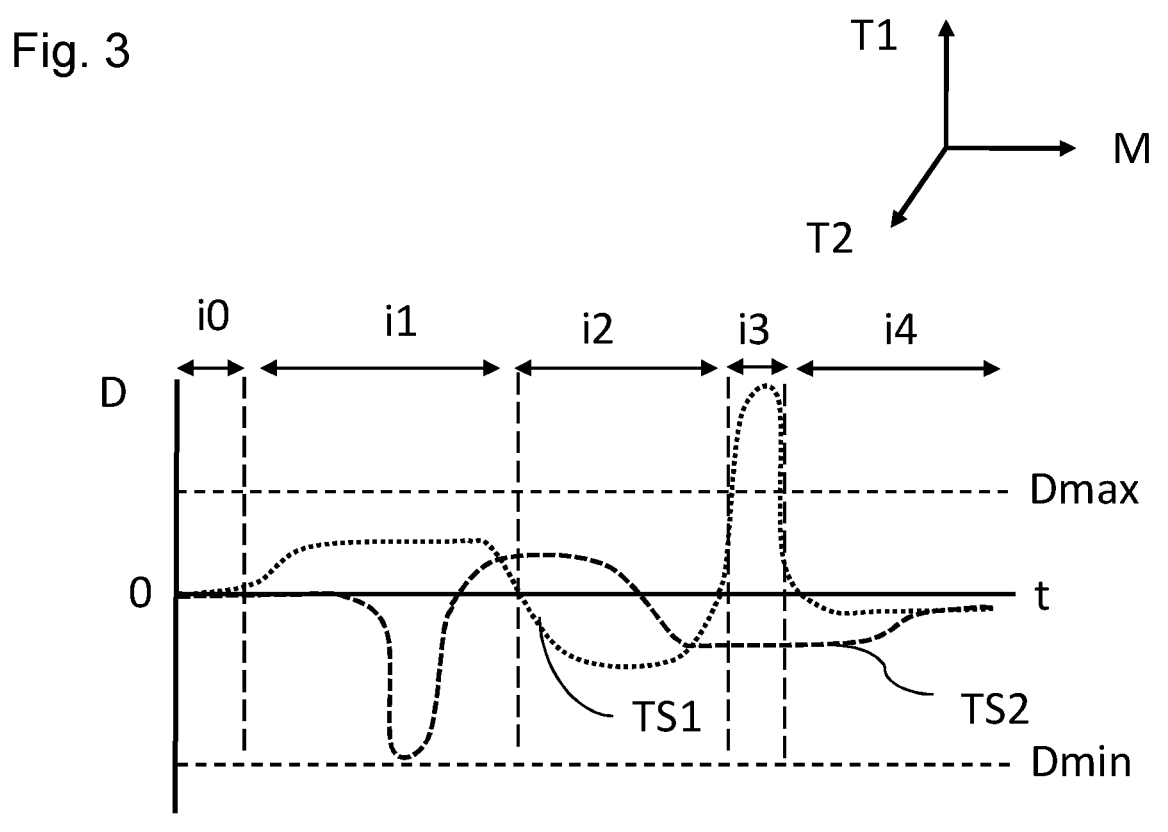

FIG. 3 schematically depicts tracking signals according to an embodiment of the present invention. An exemplary tracking signal (TS1), representative for displacements (D) of a structural element in a tracking direction perpendicular (T1) to a measurement direction (M), is depicted over time (t). On the basis of the exemplary tracking signal (TS1), five intervals (i0, i1, i2, i3, i4) can be distinguished in this example. Here, the onset of the tracking signal (TS1) is defined to have zero displacement. During the zero interval (i0), no displacements are determined in the tracking direction (T1). A positive displacement is determined in two intervals (i1, i3), and a negative displacement in (i2, i4). In i0, no displacement has occurred in the tracking direction (T1) and the measurement signal is representative for vibrations of the structural element. In the next interval (i1), the measured measurement signal may deviate, due to displacement of the structural element. As a result, the measurement beam may be reflected by another part of the structural element. The measurement signal may be corrected in dependence of determined displacement.

The OCT device may also be adapted to compensate for the determined displacement in this interval (i1) by directing a measurement beam of the OCT device towards the part of the structural element, such that the measurement beam remains reflected by the same part of structural element and measurements may be performed continuously.

During the next interval (i2), a displacement is determined in the negative tracking direction (T1) and the measurement signal may be corrected accordingly.

In interval three (i3), a displacement determined in the tracking signal (TS1) exceeds a predetermined threshold value (Dmax). This threshold value may represent a maximum adaptation of the OCT device for compensation of displacements and/or a maximum correction that can be applied on the measured vibrographic signal. The measurement beam may also have been moved away from the structural element, while the measurement beam is not reflected by another structural element within an imaging depth and field of view of the OCT device (2). Additionally or alternatively, the predetermined threshold value may comprise other properties, such as a maximum speed of the displacement (D), obtained by derivation of the tracking signal (TS1).

During interval three (i3), the measurement signal may not provide valuable information and is therefore discarded. The signal may be discarded by deletion, or the measurement beam (22) of the device (2) may be deactivated upon exceeding the threshold value (Dmax).

Then, in the last interval (i4), the displacement is less than the threshold value (Dmax), the discarding of the signal is stopped and the measurement signal may be adjusted as in interval two (i2).

The tracking system may be arranged to measure a component (TS1) of the tracking signal representative for displacement of the structural element in a first tracking direction (T1) and a component (TS2) of the tracking signal representative for displacement of the structural element in a second tracking direction (T2) perpendicular to the first tracking direction (T1) and the measurement direction (M). The tracking system may also be arranged to measure a tracking signal representative for displacements of the structural element in a third tracking direction, transverse to the first and the second tracking direction. As such, 3-dimensional tracking may be performed by the tracking system. In an even further embodiment, the third tracking direction is arranged perpendicularly to the first and the second tracking direction, such that the three tracking directions span an orthogonal 3-dimensional tracking space. A third tracking direction may be measured with the tracking system similar to the first and/or second tracking direction.

Multiple threshold values (Dmax, Dmin) may be predetermined for the respective directions (T1, T2) and/or for positive and negative versions thereof.

Figures 4A, 4B, 4C:
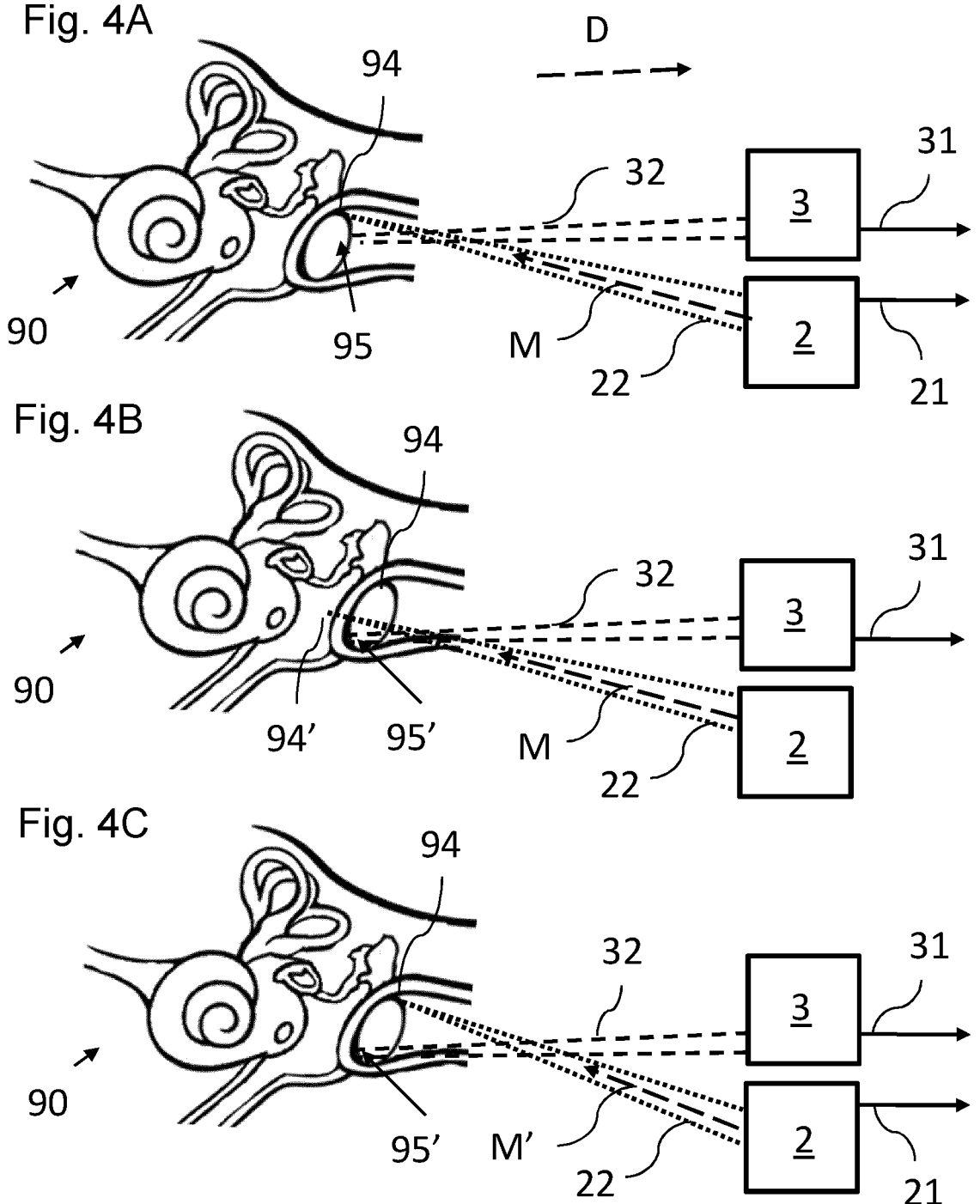
FIGS. 4A-4C schematically depict an embodiment of a measurement system according the present invention, before and after displacement of the structural element.

Different types of adjustment of the measurement signal may be combined. FIGS. 4A-4C schematically depict an embodiment of a measurement system according the present invention, before and after displacement of the structural element.

In FIG. 4A, a measurement beam (22) is directed towards a structural element (94) and a vibrographic measurement signal (21) is measured by the OCT device (2). A tracking signal (31) is measured by the tracking system (3), in dependence of a tracking beam (32) from the tracking location (95).

Upon a displacement (D) of the ear (90), as shown in FIG. 4B, the structural element (94) is not measured by the measurement beam (22). Instead, a random location (94') is measured. The vibrographic measurement signal (21) is discarded. The displacement from tracking location (95) towards new tracking location (95') is represented in the tracking signal (31).

In FIG. 4C, the OCT device (2) is adapted, such that a measurement signal (21) representative for the vibrations of the structural element in a measurement direction (M') is measured. The tracking system (3) continues to measure the new tracking location (95'). Alternatively, the tracking system (3) may also be adapted to measure tracking location (95) again.

Figure 5A:
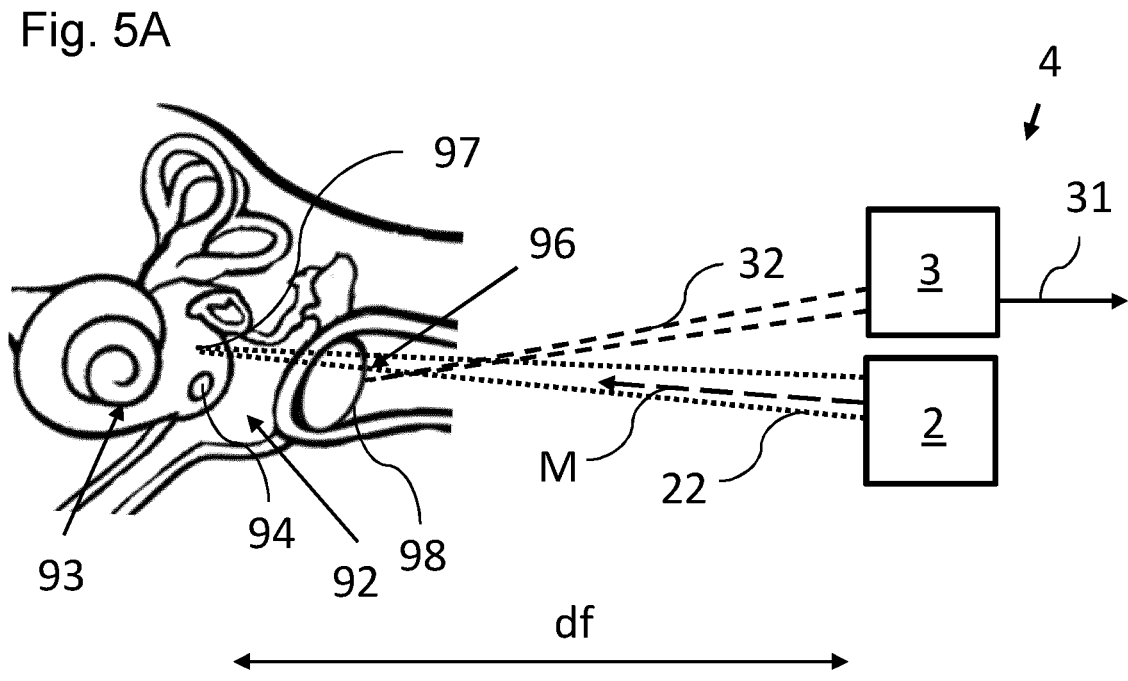
FIGS. 5A-5B schematically depict an embodiment of a measurement system according to the present invention, wherein the OCT device is configured to measure a second measurement signal representative for vibrations of a second structural element.
Figure 5B:
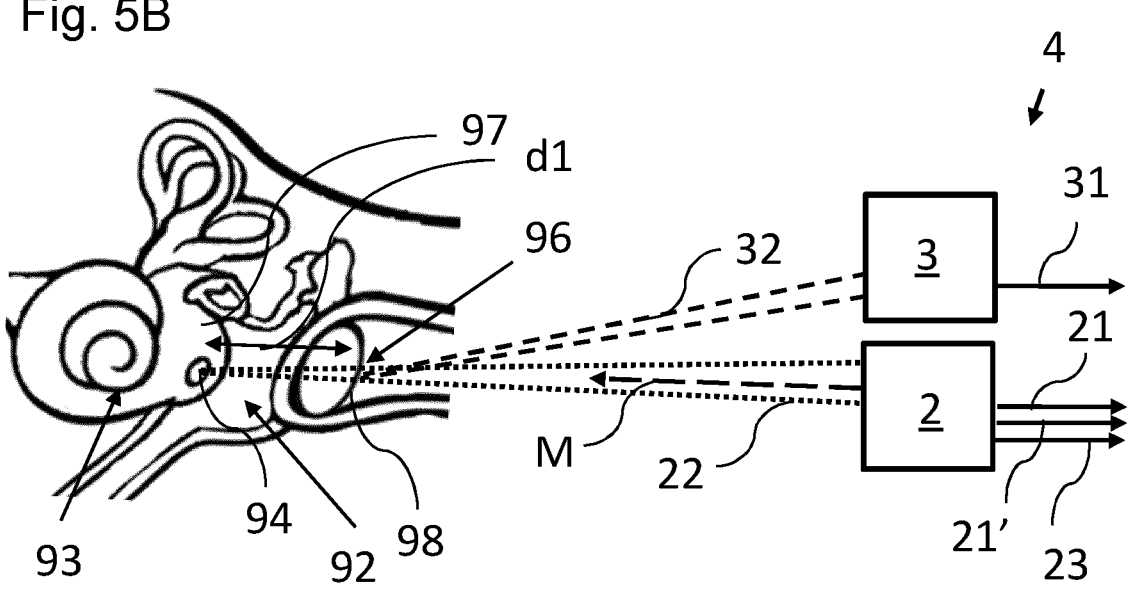

FIGS. 5A-5B schematically depict an embodiment of a measurement system (4) according to the present invention. The OCT device (2) is configured to focus the measurement beam (22) on the structural element (94) upon performing the step of selecting a focusing location (97), having a reflectivity higher than the reflectivity of the structural element (94). The focusing location (97) has a predetermined positional relationship with respect to the structural element (94). The focusing location (97) may be selected manually by a user of the OCT device, or alternatively be selected by computer algorithms. Aiming the measurement beam (22) may consequently also be performed manually or automatically, for example with an aiming arrangement.

In the present embodiment, the structural element (94) is the round window, and the focusing location is a bone (97) located nearby the structural element in the inner ear.

The OCT device (2) emits a beam (22) similarly to a measurement beam, in a direction (M) aimed towards the predetermined measurement location (97), wherein an optical path length of a reference arm and/or focus the beam a is varied to optimize a signal strength of the reflected beam (22). The reflected beam (22) is then analysed, after which a focus setting is determined based on a reflected beam having a favourable signal-to-noise ration. The focus setting may, for example, be selected manually or using software algorithms.

Additionally or alternatively, a distance (df) to the focusing location may be determined on the basis of the optical path length of the measurement beam (22) and/or a reflected measurement beam received by the OCT device (2). Alternatively, the distance may be determined on the basis of structural information received in a tracking beam (32) by the tracking system (3). Using the determined distance, a focus setting can be determined for the measurement beam to focus on the structural element using the determined distance to the focusing location.

The measurement beam (22) is then adjusted to the focus on the structural element (94) using the determined focus setting, as depicted in FIG. 5B. The measurement beam may be adjusted by focusing and aiming with an aiming arrangement and/or by changing a reference distance of a reference mirror of the OCT device (2).

The OCT device (2) of the measurement system (4) is further configured to measure a second tracking signal (23), presentative for displacements of the structural element (94) with respect to a second structural element (98), by measuring a distance (d1) between the structural element (94) and a second structural element (98). The structural element (94) and the second structural element (98) are located at a distance from each other in the measurement direction (M). In use, the measurement signal (21) and the second tracking signal (23) are measured simultaneously using one measurement beam (22) in the measurement direction (M).

The structural element (94) is the round window and the second structural element (98) is the tympanic membrane. Thus, the second structural element (98) comprises the tracking location (96), and the tracking location (96) and a measurement location of the second tracking signal (23) on the second structural element (98) are the same.

The OCT device is configured to measure a second measurement signal (21') representative for vibrations of the second structural element (98).

The OCT device (2) measures the second measurement signal (21') of the second structural element (98) and the measurement signal (21) of the structural element (94) simultaneously with the same measurement beam (22) in the measurement direction (M). The tracking location (96), a measurement location of the second measurement signal (21') and a measurement location of the second tracking signal (23) on the second structural element (98) are the same. In other embodiments, the OCT device (2) may be configured to measure the second structural element (98) with a separate measurement beam and/or by moving the measurement beam (22) in different measurement directions.

In use, adjustment of the measurement signal (21) and the second measurement signal (21') is performed in dependence of the tracking signal (31) and the second tracking signal (23), simultaneously while measuring the second tracking signal (23) and the tracking signal (31).

FIGS. 6A-6B schematically depict measurement beams of an OCT device according to the embodiment of FIG. 5B. The second structural element (98) is shown parallel to the structural element (94) in FIG. 6A, and non-parallel in FIG. 6B. A measurement beam (22) is measured with the OCT device (2). The tracking system (not shown) is configured to provide a tracking signal representative for displacements of the second structural element (98), and therefore the tracking signal is also indirectly representative for displacements of the structural element (94) in a tracking direction (T). The second structural element (98) comprises the tracking location. However, the structural element (94) may not be visible by the tracking system as is may be obscured by the second structural element (98). The OCT device (2) is configured to provide a second tracking signal (23), representative for displacements of the structural element (94) with respect to the second structural element (98) in the measurement direction (M).

In use, the measurement beam (22) passes through the second structural element (98). The second tracking signal (23A) that is measured comprises extracted amplitudes of interference peaks (24) in the interference detected by the detector, obtained using an inverse Fourier transform thereof. Additionally, phases of the interference peaks (24) may be extracted as a second vibrographic measurement signal.

A distance (d1) between amplitudes in the second tracking signal (23A) is representative for displacements of the structural element (94) and the second structural element (98). Based on an initial measurement and/or previous measurement of the ear of the patient, a ground distance may be provided (d1).

Upon a displacement of the ear and/or the measurement beam (22') in the tracking direction (T), a distance (dl) may be measured, which may be compared to the ground distance (d1). If the distances differ, as shown in (23D), a displacement has occurred in the measurement direction, which may be determined with the second tracking signal. However, if the distances are equal, as shown in (23B), no displacement has occurred between the structural element (94) with respect to the second structural element (98), and displacements of the second structural element (98) may be represented in the tracking signal of the tracking system, for example as changes in dimensions of the structural element in the tracking direction, may be represented in the tracking signal.

However, rotations of the structural element (94) may be difficult to distinguish on the basis of a tracking signal alone, especially in the case of rotations around an axis of the structural element (94), as such rotations may cause relatively small displacements of the structural element (94) in the tracking direction (T). Here, a distance (dr) is measured in the second tracking signal (23C, 23E), which is smaller than or larger than the ground distance (d1). As such, it becomes possible to reliably determine rotational displacements of the structural element (94) with respect to the OCT device (2) and precise tracking of a structural element (94) may be possible during vibrographic measurements, even if the structural element is located in a different plane such that it cannot be tracked directly with a tracking system.

The invention claimed is:

1. A method for tracking vibrations of a structural element of a middle or inner ear with optical coherence tomography (OCT) using a measurement system, the measurement system comprising:

an acoustic source configured to generate an acoustic stimulus to induce vibrations of the structural element;

an OCT device configured to measure a measurement signal, comprising vibrographic information representative for the vibrations of the structural element in a measurement direction; and an optical tracking system comprising a sensor arranged to measure a tracking signal representative for displacements of the structural element in at least a tracking direction perpendicular to the measurement direction, and wherein the method comprises the steps of:

a. generating the acoustic stimulus with the acoustic source to induce the vibrations of the structural element;

b. measuring the measurement signal comprising the vibrographic information representative for the vibrations of the structural element;

c. measuring the tracking signal representative for the displacements of the structural element; and d. using the tracking signal to adjust the measurement signal measured in step b;

wherein the optical tracking system comprises a video camera, thermal camera, scanning laser ophthalmoscope or OCT tracking system, wherein a sensitive wavelength range of the optical tracking system differs from a wavelength range the OCT device, wherein the wavelength range of the OCT device is selected for high transmission through the tympanic membrane, and wherein the sensitive wavelength range of the optical tracking system is selected for high reflectivity on the tympanic membrane.

2. The method according to claim 1, wherein steps b, c, and d, are performed simultaneously.

3. The method according to claim 1, wherein adjusting the measurement signal comprises correcting the measurement signal in dependence of a displacement of the structural element determined on the basis of the tracking signal.

4. The method according to claim 1, wherein adjusting the measurement signal comprises adapting the OCT device to compensate for a displacement of the structural element determined on the basis of the tracking signal.

5. The method according to claim 1, wherein adjusting the measurement signal comprises discarding a measurement signal obtained when a displacement of the structural element determined on the basis of the tracking signal exceeds a predetermined threshold value.

6. The method according to claim 1, wherein the tracking system is arranged to measure displacements of a predetermined tracking location of the ear in the tracking direction, wherein a position of the predetermined tracking location of the ear is representative for a position of the structural element in the tracking direction.

7. The method according to claim 6, wherein the predetermined tracking location of the ear is a part of the tympanic membrane.

8. The method according to claim 6, wherein the tracking system is arranged to identify the predetermined tracking location of the ear.

9. The method according to claim 1, wherein the measurement system is further configured to measure a second tracking signal, representative for displacements of the structural element with respect to a second structural element, further comprising a step of measuring the second tracking signal representative for the displacements of the structural element with respect to the second structural element.

10. The method according to claim 9, wherein the step of using the tracking signal to adjust the measurement signal is performed in further dependence of the second tracking signal.

11. The method according to claim 9, wherein the OCT device is further configured to measure the second tracking signal.

12. The method according to claim 9, wherein the measurement signal and the second tracking signal are measured simultaneously using one measurement beam.

13. The method according to claim 1, wherein the OCT device is configured to measure a second measurement signal representative for vibrations of a second structural element in the measurement direction, wherein the method comprises the step of:

measuring the second measurement signal of the second structural element.

14. The method according to claim 11, wherein the tracking system is arranged to measure displacements of a predetermined tracking location of the ear in the tracking direction, wherein a position of the predetermined tracking location of the ear is representative for a position of the structural element in the tracking direction, wherein the OCT device is configured to measure the second tracking signal by measuring a distance between the structural element and a second structural element, and wherein the second structural element comprises the tracking location.

15. The method according to claim 14, wherein the OCT device is configured to measure a second measurement signal representative for vibrations of a second structural element in the measurement direction, wherein the method comprises the step of:

measuring the second measurement signal of the second structural element, wherein a measurement location of the second measurement signal on the second structural element is the tracking location of the tracking signal or the second tracking signal on the second structural element.

16. The method according to claim 15, wherein the second structural element is the tympanic membrane.

17. A method for tracking vibrations of a structural element of a middle or inner ear with optical coherence tomography (OCT) using a measurement system, the measurement system comprising:

an acoustic source configured to generate an acoustic stimulus to induce vibrations of the structural element;

an OCT device configured to measure a measurement signal, comprising vibrographic information representative for the vibrations of the structural element in a measurement direction; and an optical tracking system comprising a sensor arranged to measure a tracking signal representative for displacements of the structural element in at least a tracking direction perpendicular to the measurement direction, and wherein the method comprises the steps of:

a. generating the acoustic stimulus with the acoustic source to induce the vibrations of the structural element:

b. measuring the measurement signal comprising the vibrographic information representative for the vibrations of the structural element;

c. measuring the tracking signal representative for the displacements of the structural element; and d. using the tracking signal to adjust the measurement signal measured in step b;

wherein step b comprises focusing a measurement beam of the OCT device on the structural element, and wherein the step of focusing comprises:

selecting a focusing location, wherein the reflectivity of the focusing location is higher than the reflectivity of the structural element and wherein the focusing location has a predetermined positional relationship with respect to the structural element;

determining a focus setting for the measurement beam with a beam reflected by the focusing location; and adjusting the measurement beam to focus on the structural element using the determined focus setting.

18. The method according to claim 17, wherein the structural element is a structural element of the inner ear, and wherein the focusing location is a bone.

19. A system for tracking of acoustic vibrations of a structural element of a middle or inner ear with optical coherence tomography (OTC), comprising:

an acoustic source configured to generate an acoustic stimulus to induce vibrations of the structural element;

an OCT device configured to measure a measurement signal comprising vibrographic information representative for the vibrations of the structural element in a measurement direction; and an optical tracking system comprising a sensor arranged to measure a tracking signal representative for displacements of the structural element in at least a tracking direction perpendicular to the measurement direction, and wherein the system is configured to perform the steps of:

a. generating the acoustic stimulus with the acoustic source to induce the vibrations of the structural element;

b. measuring the measurement signal comprising the vibrographic information representative for the vibrations of the structural element;

c. measuring the tracking signal representative for the displacements of the structural element;

d. using the tracking signal to adjust the measurement signal of step b;

wherein the optical tracking system comprises a video camera, thermal camera, scanning laser ophthalmoscope or OCT tracking system, wherein a sensitive wavelength range of the optical tracking system differs from a wavelength range the OCT device, wherein the wavelength range of the OCT device is selected for high transmission through the tympanic membrane, and wherein the sensitive wavelength range of the optical tracking system is selected for high reflectivity on the tympanic membrane.

* * * * *